United States Patent
Cavecchi et al.

(10) Patent No.: US 10,350,164 B2
(45) Date of Patent: Jul. 16, 2019

(54) PROCESS FOR PREPARING A DRY POWDER FORMULATION COMPRISING AN ANTICHOLINERGIC, A CORTICOSTEROID AND A BETA-ADRENERGIC

(71) Applicant: CHIESI FARMACEUTICI S.p.A., Parma (IT)

(72) Inventors: Alessandro Cavecchi, Parma (IT); Cristiana Merusi, Parma (IT); Fausto Pivetti, Parma (IT); Francesca Schiaretti, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/975,017

(22) Filed: May 9, 2018

(65) Prior Publication Data

US 2018/0325815 A1    Nov. 15, 2018

(30) Foreign Application Priority Data

May 11, 2017  (EP) .................................... 17170632

(51) Int. Cl.

| | |
|---|---|
| *A61K 9/00* | (2006.01) |
| *A61K 31/40* | (2006.01) |
| *A61K 9/14* | (2006.01) |
| *A61K 47/12* | (2006.01) |
| *A61K 31/167* | (2006.01) |
| *A61P 11/06* | (2006.01) |
| *A61P 11/08* | (2006.01) |
| *A61K 31/573* | (2006.01) |
| *A61K 47/26* | (2006.01) |
| *A61K 45/06* | (2006.01) |

(52) U.S. Cl.
CPC ............ *A61K 9/0075* (2013.01); *A61K 9/145* (2013.01); *A61K 31/167* (2013.01); *A61K 31/40* (2013.01); *A61K 31/573* (2013.01); *A61K 45/06* (2013.01); *A61K 47/12* (2013.01); *A61K 47/26* (2013.01); *A61P 11/06* (2018.01); *A61P 11/08* (2018.01); *A61K 2300/00* (2013.01)

(58) Field of Classification Search
CPC ...... A61K 9/0075; A61K 45/06; A61K 47/12; A61K 47/26; A61K 31/40; A61P 11/08
See application file for complete search history.

(56) References Cited

U.S. PATENT DOCUMENTS 7,186,401 B2 * 3/2007 Keller ................. A61K 9/0075
424/43

FOREIGN PATENT DOCUMENTS

| WO | 01/78693 | 10/2001 |
|---|---|---|
| WO | 2011/076843 | 6/2011 |
| WO | 2015/004243 | 1/2015 |
| WO | 2017/085004 | 5/2017 |
| WO | 2017/085007 | 5/2017 |

OTHER PUBLICATIONS

European Search Report in Application No. 17170632.8 dated Sep. 13, 2017, 8 pages.
International Search Report and Written Opinion dated Jul. 10, 2018 in PCT/EP2018/061955.

* cited by examiner

*Primary Examiner* — Carlos A Azpuru
(74) *Attorney, Agent, or Firm* — Oblon, McClelland, Maier & Neustadt, L.L.P.

(57) ABSTRACT

A process for preparing a dry powder formulation for inhalation comprising a combination of an anti-cholinergic, a long-acting beta$_2$-adrenoceptor agonist, and, optionally, an inhaled corticosteroid, is provided.

20 Claims, No Drawings

PROCESS FOR PREPARING A DRY POWDER FORMULATION COMPRISING AN ANTICHOLINERGIC, A CORTICOSTEROID AND A BETA-ADRENERGIC

CROSS REFERENCES TO RELATED APPLICATIONS

This application claims priority to European Patent Application No. 17170632.8 filed on May 11, 2017, which is incorporated herein by reference in its entirety.

BACKGROUND OF THE INVENTION

Field of the Invention

The present invention relates to powder formulations for administration by inhalation by means of a dry powder inhaler. In particular, the present invention relates to processes for preparing a dry powder formulation comprising a combination of an anticholinergic, a beta$_2$-adrenoceptor agonist, and an inhaled corticosteroid.

Discussion of the Background

Respiratory diseases are a common and important cause of illness and death around the world. In fact, many people are affected by inflammatory and/or obstructive lung diseases, a category characterized by inflamed and easily collapsible airways, obstruction to airflow, problems exhaling and frequent medical clinic visits and hospitalizations. Types of inflammatory and/or obstructive lung disease include asthma, bronchiectasis, bronchitis and chronic obstructive pulmonary disease (COPD).

In particular, chronic obstructive pulmonary disease (COPD) is a multi-component disease characterized by airflow limitation and airway inflammation. Exacerbations of COPD have a considerable impact on the quality of life, daily activities and general well-being of patients and are a great burden on the health system. Thus, the aim of COPD management includes not only relieving symptoms and preventing disease progression but also preventing and treating exacerbations.

While available therapies improve clinical symptoms and decrease airway inflammation, they do not unequivocally slow long-term progression or address all disease components. With the burden of COPD continuing to increase, research into new and improved treatment strategies to optimize pharmacotherapy is ongoing, and in particular, combination therapies, with a view to their complementary modes of action enabling multiple components of the disease to be addressed. Evidence from recent clinical trials indicates that triple therapy, combining an anticholinergic with an inhaled corticosteroid, and a long-acting $\beta_2$-adrenoceptor agonist, may provide clinical benefits additional to those associated with each treatment alone in patients with more severe COPD.

Currently, there are several recommended classes of therapy for COPD, of which bronchodilators such as $\beta_2$-agonists and anti-cholinergics are the mainstay of symptom management in mild and moderate diseases, prescribed on an as-needed basis for mild COPD and as a maintenance therapy for moderate COPD.

Said bronchodilators are efficiently administered by inhalation, thus increasing the therapeutic index and reducing side effects of the active material.

For the treatment of more severe COPD, guidelines recommend the addition of inhaled corticosteroids (ICSs) to long-acting bronchodilator therapy. Combinations of therapies have been investigated with a view to their complementary modes of action enabling multiple components of the disease to be addressed. Data from recent clinical trials indicates that triple therapy, combining an anticholinergic with a long-acting $\beta_2$-agonist (LABA), and an ICS, may provide clinical benefits additional to those associated with each treatment alone in patients with moderate to severe forms of respiratory diseases, particular moderate to severe COPD.

An interesting triple combination, presently under investigation, includes:

(i) formoterol, particularly its fumarate salt (hereinafter indicated as FF), a long acting beta-2 adrenergic receptor agonist, currently used clinically in the treatment of asthma, COPD and related disorders;

(ii) glycopyrronium bromide, an anticholinergic recently approved for the maintenance treatment of COPD; and (iii) beclometasone dipropionate (BDP) a potent anti-inflammatory corticosteroid, available under a wide number of brands for the prophylaxis and/or treatment of asthma and other respiratory disorders.

However, despite their popularity, pMDI formulation may have some disadvantages in particular in elderly and pediatric patients, mostly due to their difficulty to synchronize actuation from the device with inspiration.

Dry powder inhalers (DPIs) constitute a valid alternative to MDIs for the administration of drugs to airways.

Typically, drugs intended for inhalation as dry powders should be used in the form of micronized particles.

For example, powder formulations for inhalation by Dry Powder Inhalers (DPIs) containing all said three active ingredients in a micronized form are disclosed in WO 2015/004243, which is incorporated herein by reference in its entirety. Said formulation takes advantage of the technology platform disclosed in WO 01/78693, which is incorporated herein by reference in its entirety, entailing the use of carrier constituted of a fraction of coarse excipient particles and a fraction made of fine excipient particles and magnesium stearate. In the specification, possible processes for preparing micronized glycopyrronium bromide are described, but no preference is given. On the other hand, similarly to other anti-muscarinic agents, glycopyrronium salts may face significant stability problems, especially immediately following conventional micronization processes by milling.

In fact, glycopyrronium bromide, once micronized, has a strong tendency to aggregate and/or agglomerate, which severely hinders downstream drug processing, particularly the preparation of dry powder formulations for administration by inhalation capable of delivering a good respirable fraction.

It is therefore an object of the invention to provide process for preparing a powder formulation suitable to administer glycopyrronium bromide in combination with LABAs and ICS overcoming the problems indicated above.

SUMMARY OF THE INVENTION

Accordingly, it is one object of the present invention to provide novel processes for preparing a powder formulation suitable to administer glycopyrronium bromide in combination with LABAs and ICS overcoming the problems indicated above.

This and other objects, which will become apparent during the following detailed description, have been achieved by the inventors' discovery of the process described below.

Thus, the present invention provides a process for preparing a powder formulation for inhalation for use in a dry powder inhaler, said powder formulation comprising:

(A) a carrier, comprising:

(a) a fraction of coarse particles of a physiologically acceptable carrier having a mass diameter of at least 60 micron; and optionally (b) a fraction of fine particles comprising a physiologically acceptable excipient, wherein at least 90% of said fine particles have a volume diameter lower than 15 microns; and (B) micronized particles of glycopyrronium bromide, an inhaled corticosteroid (ICS), and optionally a long-acting $\beta_2$-agonist (LABA), as active ingredients, wherein said process comprises:

(i) preparing by co-milling microparticles consisting of glycopyrronium bromide and a first part of the ICS in ratio ranging from 80:20 to 70:30 by weight, wherein the volume diameter of said microparticles is no more than 15 microns;

(ii) mixing the carrier, the remaining part of said ICS and, optionally, the long-acting $\beta_2$-agonist to obtain a first mixture; and (iii) adding the co-milled microparticles obtained in step (i) to the first mixture obtained in step (ii), to obtain a second, final, mixture.

In a particular variant, the invention is directed to a process for preparing a powder formulation for inhalation for use in a dry powder inhaler, said powder formulation comprising:

(A) a carrier, comprising:

(a) a fraction of coarse particles of a physiologically acceptable carrier having a mass median diameter of at least 175 μm; and (b) a fraction of fine particles consisting of a mixture of 90 to 99.5 percent by weight of particles of a physiologically acceptable excipient and 0.5 to 10 percent by weight of a salt of a fatty acid, wherein at least 90% of said fine particles have a volume diameter equal to or lower than 15 microns, wherein the weight ratio of said fine particles to said coarse particles is 5:95 to 30:70; and (B) micronized particles of glycopyrronium bromide, a long-acting $\beta_2$-agonist (LABA), and an inhaled corticosteroid (ICS), as active ingredients, wherein said process comprises:

(i) preparing by co-milling microparticles consisting of glycopyrronium bromide and a first part of the ICS in a ratio ranging from 80:20 to 70:30 by weight, wherein the volume diameter of said microparticles is no more than 15 microns;

(ii) mixing the carrier, the LABA and the remaining part of said ICS in a vessel of a shaker mixer at a speed of rotation not lower than 16 r.p.m. for a time of not less than 60 minutes, to obtain a first mixture; and (iii) adding the co-milled microparticles obtained in step (i) to the first mixture obtained in step (ii), to obtain a second mixture, and blending said second mixture at a speed of rotation not higher than 16 r.p.m. for a time of not more than 40 minutes to obtain a blend.

In a preferred embodiment, the ICS is beclometasone dipropionate.

In an even more preferred embodiment, the LABA is formoterol fumarate dihydrate.

DETAILED DESCRIPTION OF THE PREFERRED EMBODIMENTS

The terms "muscarinic receptor antagonists", "antimuscarinic drugs" and "anticholinergic drugs" are synonymous.

The term "glycopyrronium bromide" refers to a bromide salt of the compound (3S,2'R), (3R,2'S)-3-[(cyclopentylhydroxyphenylacetyl)oxy]-1,1-dimethylpyrrolidinium in approximately 1:1 racemic mixture, also known as glycopyrrolate.

The term "pharmaceutically acceptable salt of formoterol" refers to a salt of the compound 2'-hydroxy-5'-[(RS)-1-hydroxy-2 {[(RS)-p-methoxy-α-methylphenethyl]amino} ethyl] formanilide.

The term "beclometasone dipropionate" refers to the compound (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[a] phenanthren-17-yl propionate.

The term "pharmaceutically acceptable salt" comprises inorganic and organic salts. Examples of organic salts include formate, acetate, trifluoroacetate, propionate, butyrate, lactate, citrate, tartrate, malate, maleate, succinate, methanesulfonate, benzenesulfonate, xinafoate, pamoate, and benzoate. Examples of inorganic salts include fluoride chloride, bromide, iodide, phosphate, nitrate and sulfate.

The term "physiologically acceptable excipient" refers to a pharmacologically-inert substance to be used as a carrier. In the context of the present invention, salts of fatty acids that are also physiologically acceptable excipients are considered as additives.

The expression "shaker mixer" refers to a versatile mixer having a wide and adjustable range of speed of rotation and inversion cycles. In said mixers, the mixing container is gimbal-mounted. Two rotation axes are positioned perpendicularly each other, and are powered independently. The turning direction and rotational speed of both axes is subject to continual and independent change. The setting of these kind of mixing process parameters is able to guarantee a high value of mixing efficiency. A typical shaker mixer is commercially available as dyna-MIX™ (Willy A. Bachofen AG, Switzerland) or 3D.S mixer (Erhard Muhr GmbH, Germany).

The expression "tumbler mixer" refers to a mixer that works with different mixing times and mixing speeds but with a typical movement characterized by the interaction of rotation, translation and inversion.

A typical tumbler mixer is commercially available as Turbula™ (Willy A. Bachofen AG, Switzerland).

The expression instant or high-shear mixer refers to mixers wherein a rotor or impeller, together with a stationary component known as a stator is used either in a tank containing the powder to be mixed to create a shear.

Typical high-shear mixers are P 100 and P 300 (Diosna GmbH, Germany), Roto Mix (IMA, Italy), and Cyclomix™ (Hosokawa Micron Group Ltd, Japan).

The term "micronized" refers to a substance having a size of few microns.

The term "coarse" refers to a substance having a size of one or few hundred microns.

In general terms, the particle size of particles is quantified by measuring a characteristic equivalent sphere diameter, known as volume diameter, by laser diffraction.

The particle size can also be quantified by measuring the mass diameter by means of suitable known instrument such as, for instance, the sieve analyzer.

The volume diameter (VD) is related to the mass diameter (MD) by the density of the particles (assuming a size independent density for the particles).

In the present application, the particle size of the active ingredients and of fraction of fine particles is expressed in terms of volume diameter, while that of the coarse particles is expressed in terms of mass diameter.

The particles have a normal (Gaussian) distribution which is defined in terms of the volume or mass median diameter (VMD or MMD) which corresponds to the volume or mass diameter of 50 percent by weight of the particles, and, optionally, in terms of volume or mass diameter of 10% and 90% of the particles, respectively.

Another common approach to define the particle size distribution is by means of three values: (i) the median diameter d(0.5) which is the diameter where 50% of the distribution is above and 50% is below; (ii) d(0.9), where 90% of the distribution is below this value; an (iii) d(0.1), where 10% of the distribution is below this value.

The span is the width of the distribution based on the 10%, 50% and 90% quantile and is calculated according to the formula.

$$\text{Span} = \frac{D[v, 0.9] - D[v, 0.1]}{D[v, 0.5]}$$

In general terms, particles having the same or a similar VMD or MMD can have a different particle size distribution, and in particular a different width of the Gaussian distribution as represented by the d(0.1) and d(0.9) values.

Upon aerosolization, the particle size is expressed as mass aerodynamic diameter (MAD), while the particle size distribution is expressed in terms of mass median aerodynamic diameter (MMAD) and Geometric Standard Deviation (GSD). The MAD indicates the capability of the particles of being transported suspended in an air stream. The MMAD corresponds to the mass aerodynamic diameter of 50 percent by weight of the particles.

In the final formulation the particle size of the active ingredients can be determined by scanning electron microscopy according to known methods.

The term "hard pellets" refers to spherical or semispherical units whose core is made of coarse excipient particles.

The term "spheronization" refers to the process of rounding off of the particles which occurs during the treatment.

The term "good flowability" refers to a formulation that is easy handled during the manufacturing process and is able of ensuring an accurate and reproducible delivery of the therapeutically effective dose.

Flow characteristics can be evaluated by different tests such as angle of repose, Carr's index, Hausner ratio or flow rate through an orifice.

In the context of the present application the flow properties were tested by measuring the flow rate through an orifice according to the method described in the European Pharmacopeia (Eur. Ph.) 8.6, $8^{th}$ Edition, which is incorporated herein by reference in its entirety. The expression "good homogeneity" refers to a powder wherein, upon mixing, the uniformity of distribution of a component, expressed as coefficient of variation (CV) also known as relative standard deviation (RSD), is less than 5.0%. It is usually determined according to known methods, for instance by taking samples from different parts of the powder and testing the component by HPLC or other equivalent analytical methods.

The expression "respirable fraction" refers to an index of the percentage of active particles which would reach the lungs in a patient.

The respirable fraction is evaluated using a suitable in vitro apparatus such as Andersen Cascade Impactor (ACI), Multi Stage Liquid Impinger (MLSI) or Next Generation Impactor (NGI), according to procedures reported in common Pharmacopoeias, in particular in European Pharmacopeia (Eur. Ph.) 8.4, $8^{th}$ Edition, which is incorporated herein by reference in its entirety. It is calculated by the percentage ratio of the fine particle mass (formerly fine particle dose) to the delivered dose.

The delivered dose is calculated from the cumulative deposition in the apparatus, while the fine particle mass is calculated from the deposition of particles having a diameter <5.0 microns.

Typically, a respirable fraction higher than 30% is considered an index of good aerosol performances.

A formulation is defined as "extrafine formulation" when, upon inhalation, the active ingredients are delivered with a fraction of particles having a size equal to or lower than 2.0 microns, equal to or higher than 20%.

The term "mid FPF" refers to the fraction of delivered dose having a particle size comprised between 2.0 and 5.0.

The expression "physically stable in the device before use" refers to a formulation wherein the active particles do not substantially segregate and/or detach from the surface of the carrier particles both during manufacturing of the dry powder and in the delivery device before use. The tendency to segregate can be evaluated according to Staniforth et al. J. Pharm. Pharmacol. 34,700-706, 1982, which is incorporated herein by reference in its entirety, and it is considered acceptable if the distribution of the active ingredient in the powder formulation after the test, expressed as relative standard deviation (RSD), does not change significantly with respect to that of the formulation before the test.

The expression "chemically stable" refers to a formulation that, upon storage, meets the requirements of the EMEA Guideline CPMP/QWP/122/02, which is incorporated herein by reference in its entirety, referring to 'Stability Testing of Existing Active Substances and Related Finished Products'.

The term "surface coating" refers to the covering of the surface of the carrier particles by forming a film of magnesium stearate around said particles. The thickness of the film has been estimated by X-ray photoelectron spectroscopy (XPS) to be approximately of less than 10 nm. The percentage of surface coating indicates the extent by which magnesum stearate coats the surface of all the carrier particles.

The term "prevention" means an approach for reducing the risk of onset of a disease.

The term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. The term can also mean prolonging survival as compared to expected survival if not receiving treatment.

According to the Global Initiative for Asthma (GINA) which is incorporated herein by reference in its entirety, "uncontrolled persistent asthma" is defined as a form characterized by daily symptoms, frequent exacerbations, frequent nocturnal asthma symptoms, limitation of physical activities, forced expiratory volume in one second ($FEV_1$) equal to or less than 80% predicted and with a variability higher than 30%. According to the Global Initiative for Asthma (GINA) guidelines 2014, which is incorporated herein by reference in its entirety, "partially uncontrolled asthma" is defined as a form characterized by less than twice a week daily symptoms, less than twice a month, nocturnal asthma symptoms, and a forced expiratory volume in one second ($FEV_1$) higher than 80% with a variability comprised between 20 and 30%.

According to the Global initiative for chronic Obstructive Pulmonary Disease (GOLD) guidelines, which is incorporated herein by reference in its entirety, "severe COPD" is a form characterized by a ratio between $FEV_1$ and the Forced Vital Capacity (FVC) lower than 0.7 and $FEV_1$ between 30% and 50% predicted. The very severe form is further characterized by chronic respiratory failure.

"Therapeutically effective dose" means the quantity of active ingredients administered at one time by inhalation upon actuation of the inhaler. Said dose may be delivered in one or more actuations, preferably one actuation (shot) of the inhaler. The term "actuation" refers to the release of active ingredients from the device by a single activation (e.g. mechanical or breath).

The term "milling" refers to any mechanical process which applies sufficient energy to the particles that is capable of breaking coarse particles down to micronized particles (microparticles) having a volume diameter not more than 15 microns.

The terms "co-milling" and "co-micronization" are used synonymously.

Wherein a numerical range is stated herein, the endpoints are included.

The present invention is directed to a process for the preparation of a dry powder formulation for use in a dry powder inhaler (DPI) comprising a carrier, and particles of glycopyrronium bromide, an inhaled corticosteroid (ICS) and, optionally, a long-acting $\beta_2$-agonist (LABA) as active ingredients, wherein, as a first step, microparticles of glycopyrronium bromide and an ICS in a certain ratio are prepared by co-milling.

Examples of LABAs, that may be present in form of pharmaceutically acceptable salts and/or solvates thereof, include formoterol, salmeterol, indacaterol, olodaterol, vilanterol, and the ultra-long-acting β2-adrenoreceptor agonist (uLABA) compound quoted with the code AZD3199.

Examples of ICS, that may be anhydrous or present in form of hydrates, include beclometasone dipropionate and its monohydrate form, budesonide, fluticasone propionate, fluticasone furoate, and mometasone furoate.

Preferably, the ICS is beclometasone dipropionate. More preferably, the LABA is formoterol fumarate dihydrate.

The microparticles made of glycopyrronium bromide and a first part of ICS are obtained by co-milling.

Advantageously, the two active ingredients are pre-mixed before being subjected to co-milling in order to achieve a homogeneous mixture, using apparatus and according to conditions known to the skilled person.

Advantageously, the ratio of glycopyrronium bromide to the ICS in the co-milling step is from 80:20 to 70:30 by weight, preferably of 75:25 by weight.

For example, if a single therapeutically effective dose of glycopyrronium bromide of 25 micrograms is requested, suitable amounts of the active ingredients will be used in such a way that the ratio of glycopyrronium bromide to the first part of ICS in the microparticles will vary between 25 micrograms to 5 micrograms and 25 micrograms to 15 micrograms.

If the ICS to be delivered is BDP at single therapeutically effective dose of 100 micrograms, a suitable amount will be then added as remaining part corresponding to a single dose varying from 95 to 85 micrograms.

A wide range of milling devices and conditions are suitable.

The selection of appropriate milling conditions, for example, intensity of milling and duration, to provide the required degree of force will be within the ability of the skilled person who will understand how to arrange those milling conditions such that the milling is capable of breaking down coarse particles. Ball milling is a preferred method. Alternatively, a high pressure homogenizer may be used in which a fluid containing the particles is forced through a valve at high pressure producing conditions of high shear and turbulence. Shear forces on the particles, impacts between the particles and machine surfaces or other particles and cavitation due to acceleration of the fluid may all contribute to the fracture of the particles. Such homogenizers may be more suitable than ball mills for use in large scale preparations of the above microparticles.

Suitable homogenizers include the EmulsiFlex high pressure homogenizer which is capable of pressure up to 4000 Bar, Niro Soavi high pressure homogenizers (capable of pressures up to 2000 Bar), and the Microfluidics Microfluidiser (maximum pressure 2750 Bar). The milling step may, alternatively, involve an agitator bead mill, for example, the DYNO-mill (Willy A. Bachofen AG, Switzerland) or the Netzsch high energy media mill. The Mechano-Fusion system (Hosokawa Micron Ltd) and the Hybridizer (Nara) are also suitable for use with the invention. Other possible milling devices include air jet mills, spiral jet mills, pin mills, hammer mills, knife mills and ultracentrifugal mills. In a preferred embodiment of the invention, a spiral jet mill may be utilized.

After the milling step, the volume diameter of the microparticles is no more than 15 microns, advantageously no more than 12 microns, more preferably no more than 10 microns. In a preferred embodiment, 90% by weight of said microparticles may have a diameter of less than 8 microns, preferably of less than 7 microns, the volume median diameter may be comprised between 1.0 and 3.0 microns, and no more than 10% of said microparticles may have a volume diameter lower than 0.6 microns.

The carrier (A) comprises a fraction of coarse excipient particles (a) and a fraction of fine particles (b).

The coarse excipient particles of the fraction (a) must have a mass diameter equal to or higher than 60 microns, preferably equal to or higher than 90 microns, more preferably equal to or higher than 175 microns.

Advantageously, all the coarse particles have a mass diameter in the range comprised between 40 and 600 microns.

In certain embodiments of the invention, the mass diameter of said coarse particles might be between 60 and 90 microns. In other embodiments, between 90 and 150 microns or between 150 and 500 microns. Preferably, the mass diameter is comprised between 200 and 400 microns.

In a preferred embodiment of the invention, the mass diameter of the coarse particles is comprised between 210 and 360 microns.

In general, the skilled person shall select the most appropriate size of the coarse excipient particles if commercially available or by sieving, using a proper classifier.

Advantageously, the coarse excipient particles may have a relatively highly fissured surface, that is, on which there are clefts and valleys and other recessed regions, referred to herein collectively as fissures. The "relatively highly fissured" coarse particles can be defined in terms of fissure index and/or rugosity coefficient as described in WO 01/78695, which is incorporated herein by reference in its entirety, in particular from page 15, line 28, to page 17, line 26, and WO 01/78693, which is incorporated herein by reference in its entirety, in particular from page 12, line 16, to page 14, line 11, and they could be characterized according to the description therein reported. Advantageously, the fissure index of said coarse particles is of at least 1.25, preferably of at least 1.5, more preferably of at least 2.0. Said coarse particles may also be characterized in terms of tapped density or total intrusion volume measured as reported in WO 01/78695, which is incorporated herein by reference in its entirety.

The tapped density of said coarse particles may advantageously be less than 0.8 g/cm$^3$, preferably from 0.8 to 0.5 g/cm$^3$. The total intrusion volume may be of at least 0.8 cm$^3$, preferably at least 0.9 cm$^3$.

The fraction of fine particles (b) comprises particles of a physiologically acceptable excipient wherein at least 90% of said particles have a volume diameter lower than 15 microns, preferably equal to or lower than 12 microns.

In a preferred variant, the fraction of fine particles (b) consists of a mixture of 90 to 99.5 percent by weight of particles of a physiologically acceptable excipient and 0.5 to 10 percent by weight of a salt of a fatty acid, wherein at least 90% of said particles have a volume diameter lower than 15 microns, preferably lower than 12 microns, more preferably equal to or lower than 10 microns.

In one of the embodiment of the invention, the above mixture may be obtained by subjecting the excipient particles and the salt of the fatty acid particles to co-micronization by milling, for example in a ball mill.

In some cases, co-micronization for at least two hours may be found advantageous, although it will be appreciated that the time of treatment will generally be such that a desired size reduction is obtained. In a more preferred embodiment of the invention the particles are co-micronized by using a jet mill.

In a preferred embodiment of the invention, at least 90% of the particles of fraction (b) have a volume diameter lower than 15 microns, preferably lower than 12 microns, the volume median diameter of said particles is from 3 to 7 microns, preferably from 4 to 6 microns, and no more than 10% of said particles have a volume diameter lower than 2.5 microns, preferably lower than 2.0 microns.

In order to achieve the control of the above particle size which allows improving the flowability of the powder, a mixture of micronized excipient particles with, optionally micronized, particles of a salt of a fatty acid may be subjected to co-mixing in any suitable mixer preferably for at least one hour, more preferably for at least two hours or in a high-energy mixer for more than 30 minutes, preferably for at least one hour, more preferably for at least two hours; otherwise the components are subjected to co-mixing in a high-energy apparatus for a period of less than about 30 minutes, preferably less than 20 minutes as disclosed in WO 2015/004243, which is incorporated herein by reference in its entirety.

Since the co-mixing step does not alter the particle size of the fraction of said particles, the person skilled in the art shall select the suitable size of the fine particles of the physiologically acceptable excipient as well as of the salt of the fatty acid, either by sieving, by using a classifier to achieve the desired particle size distribution.

Materials of the desired particle size distribution are also commercially available.

Advantageously, the fine and coarse excipient particles may consist of any pharmacologically inert, physiologically acceptable material or combination thereof; preferred excipients are those made of crystalline sugars, in particular lactose; the most preferred are those made of α-lactose monohydrate.

Preferably, the coarse excipient particles and the fine excipient particles both consist of α-lactose monohydrate.

Advantageously, the salt of the fatty acid, which acts as an additive to improve the respirable fraction, consists of a salt of fatty acids such as lauric acid, palmitic acid, stearic acid, behenic acid, or derivatives (such as esters and salts) thereof. Specific examples of such materials are: magnesium stearate; sodium stearyl fumarate; sodium stearyl lactylate; sodium lauryl sulfate, magnesium lauryl sulfate.

The preferred salt of fatty acid is magnesium stearate.

Advantageously, when it is used as the additive, magnesium stearate may coat the surface of the excipient particles of fine fraction (b) in such a way that the extent of the surface coating is at least of 10%, more advantageously, higher than 20%.

In some embodiments, depending on the amount of magnesium stearate as well as on the processing conditions, an extent of the surface coating higher than 50%, preferably higher than 60% may be achieved.

The extent to which the magnesium stearate coats the surface of the excipient particles may be determined according to the methods disclosed in WO 2015/004243, which is incorporated herein by reference in its entirety, in particular from page 12, line 16, to page 14, line 11.

The step of mixing the coarse excipient particles (a) with the fraction of fine particles (b) is typically carried out in any suitable mixer, e.g. tumbler mixers such as Turbula™, or high shear mixers such as those available from Diosna, for at least 5 minutes, preferably for at least 30 minutes, more preferably for at least two hours.

In a general way, the skilled person shall adjust the time of mixing and the speed of rotation of the mixer to obtain a homogenous mixture.

When spheronized carrier particles are desired to obtain hard-pellets according to the definition reported above, the step of mixing shall be typically carried out for at least four hours.

In a particular embodiment, the carrier consisting of the fraction of coarse particles (a) and the fraction of fine particles (b) may be prepared by mixing any suitable mixer. For instance, if a Turbula™ mixer is utilized, the two fractions shall be mixed at a rotation speed of 11 to 45 rpm, preferably 16 to 32 rpm for a period of at least 30 minutes, preferably from 30 to 300 minutes, more preferably from 150 to 240 minutes.

In an even more particular embodiment, the carrier may be obtained by co-mixing the coarse excipient particles, the micronized excipient particles and the fatty acid salt micronized particles together in any suitable mixer. For instance, if the Turbula™ mixer is utilized, the three components shall be mixed for a time higher than 30 minutes, advantageously from 60 to 300 minutes.

The ratio between the fraction of fine particles (b) and the fraction of coarse particles (a) may be from 1:99 to 30:70% by weight, preferably from 2:98 to 20:80% by weight.

Preferably, the ratio may be from 5:95 to 15:85% by weight.

In certain embodiments, the ratio may be 10:90 by weight, while in other embodiments, the ratio may be 5:95 by weight.

If the process is carried out according to the particular variant, in step (ii), the carrier, the LABA active ingredient, and the ICS active ingredient, are loaded in the vessel of a suitable shaker mixer having a wide and adjustable range of speed of rotation and inversion cycles.

It has indeed been found that said type of mixers are particularly suitable due to their versatility. In fact, with said mixers, frequent changes in the revolution cycles can be set in order to continuously change the powder flow inside the mixing drum and create different powder flow patterns to increase mixing efficacy.

The carrier may be mixed in a shaker mixer with the remaining part of ICS and the LABA active ingredient at a speed of rotation not lower than 16 r.p.m. preferably from 16 to 32 r.p.m., for a time of not less than 60 minutes, preferably from 60 to 120 minutes.

In step (iii), the co-milled microparticles of glycopyrronium bromide and ICS are added to the above mixture, and blended at a speed of rotation not higher than 16 r.p.m., preferably 15 r.p.m. or lower, for a time of not more than 40 minutes, preferably from 20 to 40 minutes, to obtain a blend.

In a preferred embodiment of the invention, the dynaMIX™ mixer is utilized.

Optionally, the resulting mixture is sieved through a sieve. The skilled person shall select the mesh size of the sieve depending on the particle size of the coarse particles.

The blend of step (iii) is (iv) finally mixed in any suitable mixer to achieve a homogeneous distribution of the active ingredients.

The skilled person shall select the suitable mixer and adjust the time of mixing and the speed of rotation of the mixer to obtain a homogenous mixture.

Advantageously, each active ingredient is present in the formulation of the invention in a crystalline form, more preferably with a crystallinity degree higher than 95%, even more preferably higher than 98%, as determined according to known methods.

Since the powder formulation obtained with the process of the present invention should be administered to the lungs by inhalation, at least 99% of said particles of active ingredients [d(v,0.99)] shall have a volume diameter equal to or lower than 10 microns, and substantially all the particles shall have a volume diameter comprised between 8 and 0.4 microns.

Advantageously, in order to better achieve the distal tract of the respiratory tree, 90% of the micronized particles of the ICS and LABA active ingredients shall have a volume diameter lower than 6.0 microns, preferably equal to or lower than 5.0 microns, the volume median diameter shall be comprised between 1.2 and 2.5 microns, preferably between 1.3 and 2.2 microns, and no more than 10% of said shall have a diameter lower than 0.6 microns, preferably equal to or lower than 0.7 microns, more preferably equal to or lower than 0.8 microns.

It follows that the width of the particle size distribution of the particles of the ISC and LABA active ingredients, expressed as a span, shall be advantageously from 1.0 to 4.0, more advantageously from 1.2 to 3.5 According the Chew et al J Pharm Pharmaceut Sci 2002, 5, 162-168, which is incorporated herein by reference in its entirety, the span corresponds to [d (v, 0.9)−d(v,0.1)]/d(v,0.5).

The size of the particles active is determined by measuring the characteristic equivalent sphere diameter, known as volume diameter, by laser diffraction. In the reported examples, the volume diameter has been determined using a Malvern apparatus. However, other equivalent apparatus may be used.

In a preferred embodiment, the Helos Aspiros instrument (Sympatec GmbH, Clausthal-Zellerfeld, Germany) is utilized. Typical conditions are: Fraunhofer FREE or Fraunhofer HRLD algorithm, R1 (0.1/0.18-35 micron) or R2 (0.25/0.45-87.5 micron) lens, 1 bar pressure.

As for the particle size determination, a CV of ±30% for the d(v0,1) and a CV of ±20% for the d(v0,5), d(v0,9) and d(v0,99) are considered within the experimental error.

All the micronized LABA and ICS active ingredients utilized in the process according to the invention may be prepared by processing in a suitable mill according to known methods.

In one embodiment of the invention, they may be prepared by grinding using a conventional fluid energy mill such as commercially available jet mill micronizers having grinding chambers of different diameters.

Depending on the type of the apparatus and size of the batch, the person skilled in the art shall suitably adjust the milling parameters such as the operating pressure, the feeding rate and other operating conditions to achieve the desired particle size. Preferably all the micronized active ingredients are obtained without using any additive during the micronization process.

The powder formulation comprising micronized particles of glycopyrronium bromide, a LABA and an ICS as active ingredients, obtainable according to process of the invention, is physically and chemically stable, freely flowable and exhibits a good homogeneity of the active ingredients.

Moreover, the above powder formulation is able of delivering a high respirable fraction, as measured by the fine particle fraction (FPF), for all the three active ingredients.

The ratio between the carrier particles and the active ingredients will depend on the type of inhaler used and the required dose.

The powder formulations obtained with the process of the invention may be suitable for delivering a therapeutic amount of all active ingredients in one or more actuations (shots or puffs) of the inhaler.

Advantageously, said formulations shall be suitable for delivering a therapeutically effective dose of all three active ingredients comprised between 50 and 600 µg, preferably between 100 and 500 µg.

For example, the formulation shall be suitable for delivering 3-15 µg of formoterol (as fumarate dihydrate) per actuation, advantageously 4 to 13.5 µg per actuation; 25 to 240 µg of beclometasone dipropionate (BDP) per actuation, advantageously 40 to 220 µg per actuation; and 5 to 65 µg of glycopyrronium (as bromide) per actuation, advantageously 11 to 30 µg per actuation. In a particularly preferred embodiment of the invention, the formulation is suitable for delivering 3 or 6 µg or 12 µg of formoterol (as fumarate dihydrate) per actuation; 50 or 100 or 200 µg of beclometasone dipropionate per actuation; and 6.5 or 12.5 µg or 25 µg of glycopyrronium (as bromide) per actuation.

In a particular embodiment, the formulation is suitable for delivering 6 µg of formoterol (as fumarate dihydrate) per actuation, 100 µg of beclometasone dipropionate per actuation, and 12.5 µg of glycopyrronium (as bromide) per actuation.

In another embodiment, the formulation is suitable for delivering 12 µg of formoterol (as fumarate dihydrate) per actuation, 200 µg of beclometasone dipropionate per actuation, and 25 µg of glycopyrronium (as bromide) per actuation.

The dry powder formulation may be utilized with any dry powder inhaler.

Dry powder inhaler (DPIs) can be divided into two basic types:

(i) single dose inhalers, for the administration of single subdivided doses of the active compound; each single dose is usually filled in a capsule; and (ii) multidose inhalers pre-loaded with quantities of active principles sufficient for longer treatment cycles.

On the basis of the required inspiratory flow rates (l/min) which in turn are strictly depending on their design and mechanical features, DPI's are also divided in:

(i) low-resistance devices (>90 l/min);
(ii) medium-resistance devices (about 60-90 l/min);
(iii) medium-high resistance devices (about 50-60 l/min); and
(iv) high-resistance devices (less than 30 l/min).

The reported classification is generated with respect to the flow rates required to produce a pressure drop of 4 KPa (KiloPascal) in accordance with the European Pharmacopoeia (Eur Ph), which is incorporated herein by reference in its entirety.

The dry powder formulations are particularly suitable for multidose DPIs comprising a reservoir from which individual therapeutic dosages can be withdrawn on demand through actuation of the device, for example that described in WO 2004/012801, which is incorporated herein by reference in its entirety.

Other multidose devices that may be used are, for instance, Diskus™ of GlaxoSmithKline, Turbohaler™ of AstraZeneca, Twisthaler™ of Schering, Clickhaler™ of Innovata, Spiromax™ of Teva, Novolizer™ of Meda, and Genuair™ of Almirall.

Examples of marketed single dose devices include Rotohaler™ of GlaxoSmithKline, Handihaler™ of Boehringer Ingelheim, and Breezehaler™ of Novartis.

Preferably, the formulation obtained with the process of the invention is utilized with the DPI device disclosed in WO 2004/012801, which is incorporated herein by reference in its entirety, in particular from page 1, first line, to page 39, last line, or its variants disclosed in WO2016/000983, which is incorporated herein by reference in its entirety, in particular from page 1, line 5, to page 15, line 34, being particularly suitable for the delivery of extrafine formulations.

To protect the DPIs from ingress of moisture into the formulation, it may be desirable to overwrap the device in a flexible package capable of resisting moisture ingress such as that disclosed in EP 1 760 008, which is incorporated herein by reference in its entirety, in particular from page 2, paragraph [0009], to page 9, paragraph [102].

Administration of the formulation prepared according to the process of the invention is indicated for the prevention and/or treatment of chronic obstructive pulmonary disease (COPD) and asthma of all types and severity.

The formulation prepared according to the process of the invention is also indicated for the prevention and/or treatment of further respiratory disorders characterized by obstruction of the peripheral airways as a result of inflammation and presence of mucus such as chronic obstructive bronchiolitis.

In certain embodiments, said formulation is particularly suitable for the prevention and/or treatment of severe and/or very severe forms COPD, and in particular for the maintenance treatment of COPD patients with symptoms, airflow limitation and history of exacerbations.

Furthermore, it might be suitable for the prevention and/or treatment of persistent asthma and asthma in patients not controlled with medium or high doses of ICS in combination with LABAs.

Other features of the invention will become apparent in the course of the following descriptions of exemplary embodiments which are given for illustration of the invention and are not intended to be limiting thereof.

EXAMPLES

Example 1. Preparation of the Carrier

Micronized alpha-lactose monohydrate (DFE Pharma, Germany) having the following particle size was used: d(v0.1)=1.7 micron; d(v0.5)=4.3 micron; and d(v0.9)=9.8 microns. About 3388 g of said micronized alpha-lactose monohydrate mixed with about 69.17 g of magnesium stearate (Peter Greven, Germany) were fed into the vessel of a dyna-MIX™ mixer (Willy A. Bachofen AG, Germany) and mixed with fissured coarse particles of α-lactose monohydrate having a mass diameter of 212-355 microns in the ratio 10:90 percent by weight. The mixing was carried out for 240 minutes at a speed of rotation of 16 and 24 r.p.m. alternatively for the two rotation axes. The ratio between micronized alpha-lactose monohydrate and magnesium stearate is 98:2 percent by weight.

The resulting mixtures of particles is termed hereinafter the "carrier".

The extent to which the magnesium stearate (MgSt) coats the surface of the fine and coarse lactose particles was determined by water contact angle measurement, and then by applying the equation known in the literature as Cassie and Baxter according to the conditions reported in the specification. The surface coating turned out to be of 26%.

Example 2. Preparation and Characterization of the Co-Milled Microparticles

Rac-glycopyrronium bromide (rac-GB) and beclometasone dipropionate (BDP) commercially available were utilized. The crystalline active ingredients were pre-mixed in a Turbula™ mixer in a ratio 75:25 by weight, in order to achieve a homogeneous mixture. The crystalline mixture was then micronized using a spiral jet-mill MC50 (Micro-Macinazione, Lugano, Switzerland) applying the following parameters:

Powder feeding speed: 0.875 Kg/h;
Milling volumetric flow rate: 16 $nm^3/h$; and
Feeding volumetric flow rate: 8 $nm^3/h$.

For comparative purposes, crystalline rac-GB alone was micronized with the following process parameters:

Powder feeding speed: 0.875 Kg/h;
Milling volumetric flow rate: 16 $nm^3/h$; and
Feeding volumetric flow rate: 8 $nm^3/h$.

Co-micronized microparticles and reference micronized glycopyrronium bromide were exposed to the following conditions:

Thin layer (~0.5 cm) in open tray for 3 days at 30° C./65% relative humidity (RH);

Thin layer (~0.5 cm) in open tray for 4 hours at 25° C./90% RH

The following analyses were performed:

(i) particle size distribution (PSD) in terms of d(v0.1), d(v0.5) and d(v0.9) by Malvern analysis, (2) Specific Surface Area (SSA) by Brunauer-Emmett-Teller (BET) nitrogen adsorption method according to a known procedure, and (3) recrystallization of water using a Dynamic Vapour Sorption (DVS) instrument (Mettler Toledo GmbH, Switzerland). The analytical results are summarized in Table 1.

TABLE 1

|  |  | SSA (m²/g) | PSD d(v0.1) (µm) | PSD d(v0.5) (µm) | PSD D(v0.9) (µm) | Re-crystallization water (% w/w) |
| --- | --- | --- | --- | --- | --- | --- |
| Co-micronized GB/BDP | Initial | 5.8 | 0.61 | 2.07 | 5.71 | 0.19 |
|  | Open thin layer 4 hours at 25° C./90% RH | Not measured | 0.68 | 2.42 | 5.99 | Not measured |
|  | Open thin layer 3 days at 30° C./65% RH | 4.07 | 0.62 | 2.30 | 5.97 | 0.10 |
| Micronized GB | Initial | 7.31 | 0.60 | 1.54 | 3.95 | 0.12 |
|  | Open thin layer 4 hours at 25° C./90% RH | Not measured | 2.74 | 156 | 1657 | Not measured |
|  | Open thin layer 3 days at 30° C./65% RH | 1.85 | 1.00 | 3.91 | 7.59 | 0.02% |

As it can be appreciated, co-micronized microparticles show no significant variation in particle size distribution and in the other related parameters upon exposure to both conditions, while micronized GB alone experienced a significant increase of the particle size, in particular at 25° C. and 90% RH, indicating that a significant agglomeration occurred.

Example 3. Preparation of the Dry Powder Formulation

Microparticles as obtained in Example 2 were used. Micronized formoterol fumarate dihydrate having the following particle size was used: d(v0.1)=0.9 micron; d(v0.5)=2.3 micron; and d(v0.9)=4.2 micron. Beclometasone dipropionate (BDP) having the following particle size was used: d(v0.1)=0.7 micron; d(v0.5)=1.5 micron; and d(v0.9)=2.8 micron.

The carrier as obtained in Example 1 was mixed in a dyna-MIX™ mixer with formoterol fumarate dihydrate and a BDP in order to have a final therapeutic effective dose of 100 micrograms per actuation of the inhaler. The mixer was operated at a speed of rotation between 22 and 28 r.p.m. for the two rotation axes for a time of 88 minutes. Then the microparticles were added and mixed at a speed of rotation between 15 and 13 r.p.m. alternatively for the two rotation axes for a time of 36 minutes.

The resulting mixture was poured into a sieving machine available from Frewitt (Fribourg, Switzerland) equipped with a 600 micron mesh size sieve. Upon sieving, the blend was finally mixed in a in the dyna-MIX™ mixer for 60 minutes of 15 and 13 r.p.m. alternatively for the two rotation axes, to achieve a homogeneous distribution of the active ingredients.

The ratio of the active ingredients to 10 mg of the carrier is 6 micrograms (µg) of FF dihydrate (theoretical delivered dose 4.5 µg), 100 micrograms (µg) of BDP and 12.5 micrograms (µg) of glycopyrronium bromide (theoretical delivered dose 10.0 µg).

The powder formulation was characterized in terms of the uniformity of distribution of the active ingredients and aerosol performances after loading it in the multidose dry powder inhaler disclosed in WO 2004/012801, which is incorporated herein by reference in its entirety.

The uniformity of distribution of the active ingredients was evaluated by withdrawing 12 samples from different parts of the blend and evaluated by HPLC. The results (mean value±RSD) are reported in Table 2.

The evaluation of the aerosol performance was carried out using the Next Generation Impactor (NGI) according to the conditions reported in the European Pharmacopeia 8.5$^{th}$ Ed 2015, which is incorporated herein by reference in its entirety, par 2.9.18, pages 309-320. After aerosolization of 3 doses from the inhaler device, the NGI apparatus was disassembled and the amounts of drug deposited in the stages were recovered by washing with a solvent mixture and then quantified by High-Performance Liquid Chromatography (HPLC). The following parameters, were calculated: (i) the delivered dose which is the amount of drug delivered from the device recovered in the all parts of impactor; (ii) the fine particle mass (FPM) which is the amount of delivered dose having a particle size equal to or lower than 5.0 micron; (iii) the extrafine FPM which is the amount of delivered dose having a particle size equal to or lower than 2.0 micron and/or equal to or lower than 1.0 micron; (iv) the mid FPM which is the amount of delivered dose having a particle size comprised between 2.0 and 5.0 micron; (v) the fine particle fraction (FPF) which is the ratio between the fine particle mass and the delivered (dose; and vi) the MMAD. The results (mean value±S.D) are reported in Table 2.

TABLE 2

|  | Active ingredient |
| --- | --- |
|  | FF |
| Uniformity of distribution | 99.4 (±1.4) |
| Delivered Dose [µg] | 5.99 (±0.3) |
| Fine Particle Mass [µg] | 4.14 |
| Fine Particle Fraction [%] | 69.4 |
| Mid Fine Particle Mass [µg] | 1.46 |
| Extrafine Particle Mass <2 µm [µg] | 2.67 |
| Extrafine Particle Mass <1 µm [µg] | 1.19 |
| Mid Fine particle Fraction [%] | 24.4 |
| Extrafine Particle Fraction <2 µm [%] | 44.6 |
| Extrafine Particle Fraction <1 µm [%] | 19.9 |
| MMAD [µm] | 1.65 |
|  | GB |
| Uniformity of distribution | 100.8 (±1.6) |
| Delivered Dose [µg] | 11.66 (±0.4) |
| Fine Particle Mass [µg] | 7.85 |
| Fine Particle Fraction [%] | 67.2 |
| Mid Fine Particle Mass [µg] | 3.46 |
| Extrafine Particle Mass <2 µm [µg] | 4.39 |

TABLE 2-continued

|  | Active ingredient |
|---|---|
| Extrafine Particle Mass <1 μm [μg] | 1.8 |
| Mid Fine particle Fraction [%] | 29.6 |
| Extrafine Particle Fraction <2 μm [%] | 37.6 |
| Extrafine Particle Fraction <1 μm [%] | 15.4 |
| MMAD [μm] | 1.92 |
| BDP | |
| Uniformity of distribution | 101.8 (±1.1) |
| Delivered Dose [μg] | 97.4 (±3.2) |
| Fine Particle Mass [μg] | 67.6 |
| Fine Particle Fraction [%] | 69.4 |
| Mid Fine Particle Mass [μg] | 17.6 |
| Extrafine Particle Mass <2 μm [μg] | 50 |
| Extrafine Particle Mass <1 μm [μg] | 27.9 |
| Mid Fine particle Fraction [%] | 18 |
| Extrafine Particle Fraction <2 μm [%] | 51.4 |
| Extrafine Particle Fraction <1 μm [%] | 28.7 |
| MMAD [μm] | 1.25 |

From the data of Table 2, it can be appreciated that the powder formulation shows both an excellent homogeneity, and a high respirable fraction (FPF), for all the three active ingredients.

Example 4. Preparation of a Further Dry Powder Formulation

The powder formulation was prepared as described in Example 3, but the ratio of the active ingredients to 10 mg of the carrier is 6 micrograms (μg) of FF dihydrate (theoretical delivered dose 4.5 μg), 100 micrograms (μg) of BDP and 25 micrograms (μg) of glycopyrronium bromide (theoretical delivered dose 20.0 μg).

The uniformity of distribution of the active ingredients and the aerosol performances were evaluated as reported in Example 2. The results are reported in Table 3.

TABLE 3

|  | Active ingredient |
|---|---|
|  | FF |
| Uniformity of distribution | 99.6 (±1.6) |
| Delivered Dose [μg] | 4.76 (±0.2) |
| Fine Particle Mass [μg] | 3.05 |
| Fine Particle Fraction [%] | 66.3 |
| Mid Fine Particle Mass [μg] | 1.05 |
| Extrafine Particle Mass <2 μm [μg] | 2.10 |
| Extrafine Particle Mass <1 μm [μg] | 0.78 |
| Mid Fine particle Fraction [%] | 22.0 |
| Extrafine Particle Fraction <2 μm [%] | 44.1 |
| Extrafine Particle Fraction <1 μm [%] | 16.3 |
| MMAD [μm] | 1.63 |
| GB | |
| Uniformity of distribution | 101.5 (±2.5) |
| Delivered Dose [μg] | 21.30 |
| Fine Particle Mass [μg] | 10.8 |
| Fine Particle Fraction [%] | 50.7 |
| Mid Fine Particle Mass[μg] | 5.94 |
| Extrafine Particle Mass <2 μm [μg] | 5.49 |
| Extrafine Particle Mass <1 μm [μg] | 1.75 |
| Mid Fine particle Fraction [%] | 27.9 |
| Extrafine Particle Fraction <2 μm [%] | 25.8 |
| Extrafine Particle Fraction <1 μm [%] | 8.2 |
| MMAD [μm] | 2.15 |
| BDP | |
| Uniformity of distribution | 100.2 (±1.2) |
| Delivered Dose [μg] | 80.9 (±3.1) |
| Fine Particle Mass [μg] | 50.0 (±1.2) |

TABLE 3-continued

|  | Active ingredient |
|---|---|
| Fine Particle Fraction [%] | 61.8 |
| Mid Fine Particle Mass [μg] | 17.3 |
| Extrafine Particle Mass <2 μm [μg] | 32.7 |
| Extrafine Particle Mass <1 μm [μg] | 13.1 |
| Mid Fine particle Fraction [%] | 21.4 |
| Extrafine Particle Fraction <2 μm [%] | 40.3 |
| Extrafine Particle Fraction <1 μm [%] | 16.2 |
| MMAD [μm] | 1.62 |

From the data of Table 3, it can be appreciated that the powder formulation show both an excellent homogeneity, and a high respirable fraction (FPF), for all the three active ingredients.

Example 5. Determination of the Caking Tendency

It is known that moisture increases the cohesive strength between glycopyrronium bromide (GB) particles to the extent that it can cause caking. Additionally, phase transformations (i.e. crystallization of the amorphous fraction present in the micronized GB particles) triggered by ambient relative humidity (RH) above 45% can result in fusing/sintering of the GB particles causing lumps and severe caking.

A test has been performed to determine the agglomeration/caking tendency of the co-milled microparticles of the invention versus reference micronized GB. The materials were prepared as reported in Example 2.

The samples were tested at the following ambient conditions:

30% RH, 22° C.;
60% RH, 32° C.;
Transition from 30% RH, 32° C. to 60% RH, 32° C.

The experiments were performed using a Dynamic Vapour Sorption (DVS) Analyzer from Surface Measurement Systems (London, UK).

The co-milled microparticles of the invention are significantly less likely to cake compared to the reference material.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for preparing a powder formulation for inhalation for use in a dry powder inhaler, said powder formulation comprising:
    (A) a carrier, comprising:
        (a) a fraction of coarse particles of a physiologically acceptable carrier having a particle size of 60 to 500 microns; and optionally
        (b) a fraction of fine particles comprising a physiologically acceptable excipient, wherein at least 90% of all said fine particles have a volume diameter lower than 15 microns; and (B) micronized particles of glycopyrronium bromide, an inhaled corticosteroid (ICS), and, optionally, a long-acting β$_2$-agonist (LABA), as active ingredients,
wherein said process comprises:
(i) preparing by co-milling microparticles comprising glycopyrronium bromide and a first part of said ICS in a ratio ranging from 80:20 to 70:30 by weight, wherein the volume diameter of said microparticles is no more than 15 microns;
(ii) mixing said carrier, the remaining part of said ICS, and optionally said long-acting β$_2$-agonist, to obtain a first mixture; and
(iii) adding the co-milled microparticles obtained in step (i) to said first mixture obtained in step (ii), to obtain a second, final, mixture.

2. A process for preparing a powder formulation for inhalation for use in a dry powder inhaler according to claim 1, wherein said powder formulation comprises:
(A) a carrier which comprises:
(a) a fraction of coarse particles of a physiologically acceptable carrier with a mass median particle size of at least 175 microns; and
(b) a fraction of fine particles consisting of a mixture of 90 to 99.5 percent by weight of particles of a physiologically acceptable excipient and 0.5 to 10 percent by weight of a salt of a fatty acid;
wherein the weight ratio of said fine particles to said coarse particles is 5:95 to 30:70; and
(B) said active ingredients including a long-acting β$_2$-agonist;
wherein in said process:
said mixing (ii) is carried out in a vessel of a shaker mixer at a speed of rotation not lower than 16 r.p.m. for a time of not less than 60 minutes, to obtain said first mixture; and
said second mixture obtained in step (iii) is blended at a speed of rotation not higher than 16 r.p.m. for a time of not more than 40 minutes to obtain a blend.

3. A process according to claim 2, further comprising: (iv) further mixing the blend obtained in step (iii) to achieve a homogeneous distribution of said active ingredients.

4. A process according to claim 1, wherein said ICS is selected from the group consisting of beclomethasone dipropionate and its monohydrate form, budesonide, fluticasone propionate, fluticasone furoate, and mometasone furoate.

5. A process according to claim 1, wherein said LABA is selected from the group consisting of formoterol, salmeterol, indacaterol, olodaterol, and vilanterol.

6. A process according to claim 1, wherein said ICS is beclometasone dipropionate and said LABA is formoterol fumarate dihydrate.

7. A process according to claim 2, wherein said salt of said fatty acid is selected from the group consisting of magnesium stearate, sodium stearyl fumarate, sodium stearyl lactylate, sodium lauryl sulfate, and magnesium lauryl sulfate.

8. The process according to claim 7, wherein said salt of said fatty acid is magnesium stearate.

9. A process according to claim 2, wherein said mixing (ii) is performed at 16-32 r.p.m., for a time comprised between 60 and 120 minutes.

10. A process according to claim 2, wherein in step (iii) is performed for a time of 20 to 40 minutes.

11. A process according to claim 1, wherein the physiologically acceptable excipient in said coarse particles of physiologically acceptable excipient (a) is alpha-lactose monohydrate.

12. A process according to claim 1, wherein the physiologically acceptable excipient in said fine particles of physiologically acceptable excipient (b) is alpha-lactose monohydrate.

13. A process according to claim 1, wherein the physiologically acceptable excipient in said coarse particles of physiologically acceptable excipient (a) is alpha-lactose monohydrate and the physiologically acceptable excipient in said fine particles of physiologically acceptable excipient (b) is alpha-lactose monohydrate.

14. A process according to claim 1, wherein said coarse particles have a mass diameter of 210 to 360 μm.

15. A powder formulation, which is prepared by a process according to claim 1.

16. A dry powder inhaler, containing a powder formulation prepared by a process according to claim 1.

17. A method for treating a respiratory disease, comprising administering to a subject in need thereof an effective amount of a powder formulation prepared by a process according to claim 1.

18. A method according to claim 17, wherein said respiratory disease is asthma, bronchiectasis, bronchitis, or chronic obstructive pulmonary disease.

19. A method according to claim 17, wherein said respiratory disease is asthma.

20. A method according to claim 17, wherein said respiratory disease is chronic obstructive pulmonary disease.

* * * * *